United States Patent [19]

Haber et al.

[11] Patent Number: 5,094,148

[45] Date of Patent: Mar. 10, 1992

[54] PISTON STEM INSERT FOR A CARPULE BASED PISTON

[75] Inventors: Terry M. Haber, El Toro; William H. Smedley, Lake Elsinore; Clark B. Foster, Laguna Niguel; John A. Lewis, Jr., Costa Mesa, all of Calif.

[73] Assignee: Habley Medical Technology Corporation, Laguna Hills, Calif.

[21] Appl. No.: 348,836

[22] Filed: May 8, 1989

[51] Int. Cl.$^5$ .............................................. F01B 9/00
[52] U.S. Cl. .......................................... 92/29; 92/248; 92/249; 92/255; 604/218; 604/110; 403/348
[58] Field of Search ................. 92/240, 242, 245, 248, 92/249, 255, 259, 14, 29, 30; 604/218, 110, 228, 227, 226, 225, 224, 223, 222; 403/348, 349, 224, 226

[56] References Cited

U.S. PATENT DOCUMENTS

| 2,044,699 | 6/1936 | Johnson | 92/245 |
|---|---|---|---|
| 2,219,907 | 10/1940 | Ross | 403/349 |
| 2,586,068 | 2/1952 | Lockhard | 604/228 |
| 2,688,325 | 9/1954 | Lockhart | 604/220 |
| 2,693,804 | 11/1954 | Pontius | 604/228 |
| 2,722,215 | 11/1955 | Stig et al. | 604/228 |
| 2,968,141 | 5/1961 | Hart | 92/170.1 |
| 3,224,445 | 12/1965 | Melott | 604/228 |
| 3,253,592 | 5/1966 | Pechmann | 604/222 |
| 3,603,215 | 9/1971 | Leschisin | 92/240 |
| 4,493,703 | 1/1985 | Butterfield | 604/110 |
| 4,650,468 | 3/1987 | Jennings, Jr. | 604/110 |
| 4,685,910 | 8/1987 | Schweizer | 604/220 |
| 4,705,509 | 11/1987 | Stade | 604/228 |

FOREIGN PATENT DOCUMENTS

| 0160391 | 10/1952 | Australia | 604/228 |
|---|---|---|---|
| 0308040 | 3/1989 | European Pat. Off. | 604/110 |
| 1029985 | 5/1958 | Fed. Rep. of Germany | 604/222 |
| 2031841 | 4/1973 | Fed. Rep. of Germany | 604/228 |
| 2728133 | 5/1979 | Fed. Rep. of Germany | 403/349 |
| 959837 | 4/1950 | France | 604/222 |
| 1117356 | 5/1956 | France | 604/228 |
| 358196 | 10/1957 | Switzerland | 604/228 |
| 0848832 | 7/1981 | U.S.S.R. | 403/349 |
| 718150 | 11/1954 | United Kingdom | 604/218 |
| 0741604 | 12/1955 | United Kingdom | 604/228 |
| 0829724 | 3/1960 | United Kingdom | 604/228 |
| 2068235 | 8/1981 | United Kingdom | 604/218 |

Primary Examiner—Edward K. Look
Assistant Examiner—Thomas Denion
Attorney, Agent, or Firm—Hawes & Fischer

[57] ABSTRACT

A piston stem insert to be received within a hollow receptacle that is molded at the interior of a carpule based piston, so that a piston stem may be easily attached to and detached from the piston by way of the insert. In a first embodiment of the invention, a set of flexible, anti-displacement wings extend radially from the insert to releasable and frictionally engage the inside walls of a carpule, so as to prevent an inadvertent and premature displacement of the piston through the carpule. In a second embodiment, a set of anti-rotation wings extend radially from the piston stem insert to be received within respective cavities of the receptacle that are shaped so that the wings may be rotated in a single (e.g. clockwise) direction but blocked from rotation in an opposite direction. In a third embodiment, the receptacle of the piston is sized and shaped relative to the anti-rotation wings, such that said wings will be automatically aligned for receipt within the cavities of the receptable during the installation of the insert.

12 Claims, 3 Drawing Sheets

PISTON STEM INSERT FOR A CARPULE BASED PISTON

BACKGROUND OF THE INVENTION

1. Field of the Invention

This invention relates to a piston stem insert for a carpule based piston by which a piston stem can be easily and reliably attached to or detached from the piston without damaging the piston or affecting its ability to be moved through the carpule.

2. Background Art

It is known within the relevant art to locate a piston stem insert within a piston body so that a piston stem can be attached to (or removed from) the piston for controlling the movement of the piston through a fluid filled cylinder, such as a medication carpule. However, there are certain unresolved problems that are associated with the interconnection of a conventional piston stem insert and a piston stem which have resulted in damage to the piston and/or prevented an easy detachment and removal of the piston stem from the piston.

More particularly, a piston stem which is screwed down too tightly against its piston stem insert is known to drive the insert inwardly through the piston. As a result, the piston might swell, crack or be subjected to some form of damage. The frictional force generated between the piston and the carpule through which said piston is to slide will be increased as the size of the piston increases. Consequently, a greater force will be required to drive an expanded or swelled piston through its carpule for explusing the fluid contents of such carpule. Moreover, the piston stem can be so tightly connected to the piston stem insert that disconnecting the stem from the insert becomes undesirably difficult. That is, the combination piston stem and insert may rotate freely relative to a piston that is split or cracked. Thus, there may be no easy way to rotate the piston stem out of engagement from its piston stem insert when it is desirable to remove the stem for disposal.

Yet another problem which has been experienced by conventional carpule based pistons occurs as the carpule, in which the piston and piston stem insert are carried, is subjected to increased atmospheric pressure, such as at a high elevation. The atmospheric pressure at such high elevation has been known to prematurely and inadvertently displace the piston through the carpule. In some cases, the piston is pushed proximally and completely out of the carpule while the carpule is still in its as-packaged configuration. The unintended spillage of fluid from a carpule whose piston has been prematurely removed would render the carpule unusable and subject to disposal and waste.

SUMMARY OF THE INVENTION

In general terms, a piston stem insert is disclosed having a first end to be received at a receptacle that is molded into a carpule based piston and an opposite end to be connected to a piston stem so that the movement of the piston through its carpule can be selectively controlled. In a first embodiment of the invention, a plurality of flexible wings project radially outward from the insert to engage the inside walls of the carpule. The friction created between the radially extending wings and the carpule prevents an inadvertent displacement (and possible removal) of the piston through the carpule. However, when it is desired to advance the piston through the carpule to expulse the fluid therefrom, the flexible wings may be rotated at respective hinges thereof by a bearing surface which projects from the piston stem so that said wings will be moved out of contact with the carpule, whereby to permit a relocation of the piston.

In a second embodiment of the invention, a plurality of wings extend radially outward from the first end of the piston stem insert to be received within respective radially extending cavities of the piston receptacle. Each of the cavities is provided with a first wall having a rounded shoulder that is adapted to permit a rotation of the wings out of their respective cavities and into adjacent cavities when the piston stem is rotated in a first (i.e. clockwise) direction to attach the piston stem to the piston stem insert. Each of the cavities is also provided with an opposite wall having a squared shoulder that is adapted to block the rotation of the wings out of their respective cavities when the piston stem is rotated in an opposite (i.e. counterclockwise) direction to detach the piston stem from the insert.

In a third embodiment of the invention, the cavities of the piston receptacle are sized so as to be larger than the wings which are to be received therewithin. Accordingly, regions of the piston that are located between adjacent cavities of the receptacle are of reduced size to form relatively narrow teeth. The narrow teeth are adapted to automatically realign (i.e. rotate) the wings into receipt by the cavities in the event that the wings are otherwise aligned with the teeth when the first end of the piston stem insert is being received at the receptacle during the installation of said insert.

DESCRIPTION OF THE PREFERRED EMBODIMENT

Figure 1:
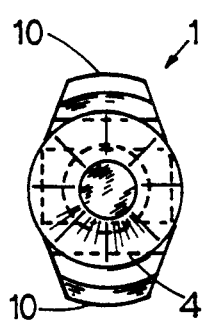
FIG. 1 is a top view of a piston stem insert which forms a first embodiment of the present invention.
Figure 2:
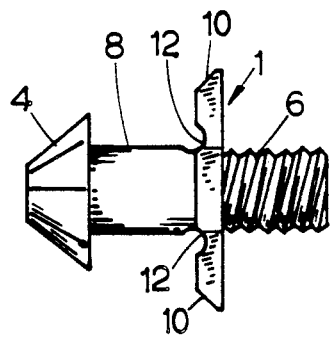
FIG. 2 is a side view of the piston stem insert of FIG. 1.
Figure 3:
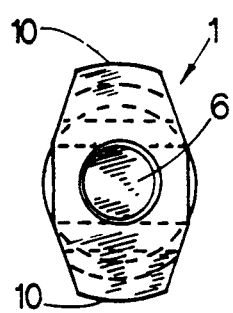
FIG. 3 is a bottom view of the piston stem insert of FIG. 1.

A piston stem insert 1 that is to be attached to a carpule based piston 2 and forms a first embodiment of the present invention is described while referring to FIGS. 1–6 of the drawings. As is best shown in FIGS. 1–3, piston stem insert 1 includes a plug or head 4 formed at one end thereof and a screw threaded rod 6 formed at the opposite end. As will be described hereinafter when referring to FIGS. 4–6, the head 4 of insert 1 is sized to be received within and retained by a receptacle (designated 14 in FIG. 4) that is molded within the piston 2, and the screw threaded rod 6 is adapted to be mated to a correspondingly screw threaded piston stem (designated 30 in FIG. 6). A cylindrical shank 8 extends between the head 4 and threaded rod 6 of insert 1. Projecting radially outward and in opposite directions from shank 8 is a pair of wings 10. Although a pair of wings 10 is shown and described, it is to be understood that any number of such wings may project radially outward from the shank 8.

It is preferable that insert 1 be manufactured from a material which will permit the wings 10 of shank 8 to flex or pivot relative to the shank in response to an axially directed force applied to said wings 10. By way of example only, insert 1 may be manufactured from a plastic-like material known as Delrin. To minimize the force necessary to cause wings 10 to pivot, material is removed from the intersections of the wings 10 with the shank 8 so as to form relatively narrow hinges 12 around which the wings may rotate. The important advantage achieved by forming insert 1 with flexible wings 10 will soon be described.

Figure 4:
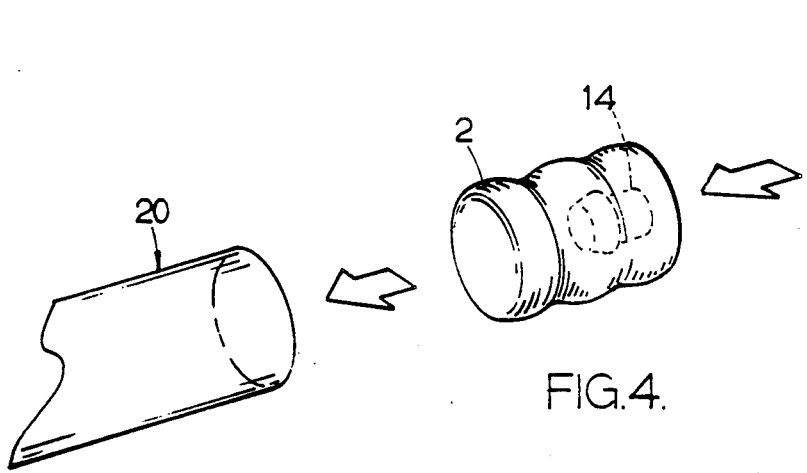
FIG. 4 is an exploded view to illustrate the interconnection of a carpule, a piston and the piston stem insert of FIG. 1.
Figure 5:
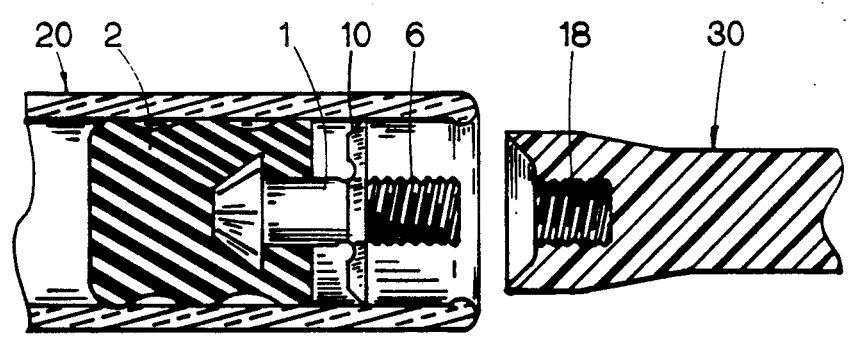
FIG. 5 illustrates the location of the piston stem insert within the carpule of FIG. 4 to prevent a displacement of the piston through said carpule.

FIG. 4 of the drawings is an exploded view representing the interconnection of the piston stem insert 1 with an associated piston 2 and a carpule 20. Carpule 20 is of conventional design and is typically filled with a fluid medication, or the like, that is to be expulsed, under pressure, as the piston is driven axially therethrough. Piston 2 includes a hollow receptacle 14 which is molded therewithin to receive and retain the head 4 of insert 1. As is best shown in FIG. 5 of the drawings, with the carpule 20 in the as-packaged configuration, the piston 2 is initially located at the proximal end of said carpule 20, such that the threaded rod 6 is aligned for engagement to a correspondingly threaded receptacle 18 of an elongated piston stem 30. In the as-packaged configuration, the radially extending wings 10 of insert 1 contact the inside walls of carpule 20 so as to form a relatively tight friction fit therewith. The frictional engagement of wings 10 to carpule 20 act to anchor the piston 2 at the proximal end of said carpule, whereby to prevent an axial displacement and inadvertent removal (i.e. popping out) of the piston 20 from the carpule, should the carpule be exposed to an increased atmospheric pressure (e.g. such as, for example, when the carpule is stored in or shipped through a geographic region characterized by a high elevation).

Figure 6:
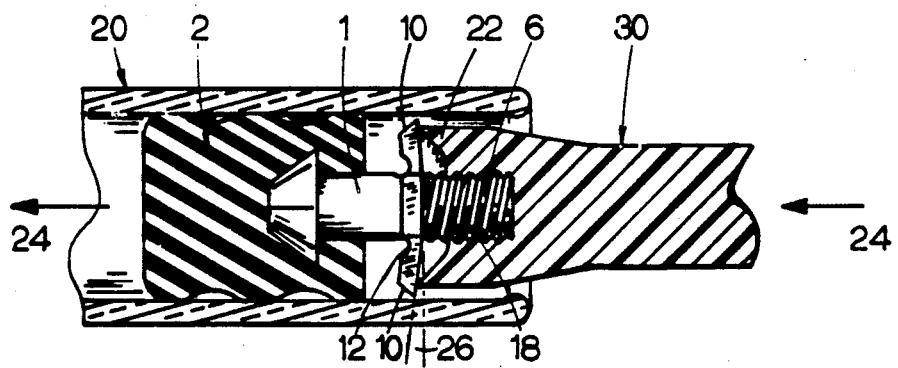
FIG. 6 shows the connection of a piston stem to the piston stem insert to permit a displacement of the piston of FIG. 5 through the carpule.

In FIG. 6 of the drawings, and with the carpule 20 in the activated configuration, the piston 2 of said carpule is interconnected with the piston stem 30 via piston stem insert 1. That is, the screw threaded rod 6 of insert 1 is received in and mated to the screw threaded receptacle 18 of piston stem 30. Piston stem 30 is preferably provided with a bearing surface 22 which is aligned to engage the wings 10 of insert 1, whereby said wings are pivoted (represented by the angle 26) at their respective hinges 12 and rotated out of engagement with the carpule 20. Therefore, an axial pushing force applied to piston stem 30 (in the direction of the reference arrow 24) can be efficiently transferred to insert 1 at the wings 10 thereof. In the example shown, the bearing surface 22 of piston stem 30 is a distally flared head that engages the wings 10 of insert 10. Of course, the shape of the bearing surface 22 can be changed so long as an axial force applied to piston stem 30 will be transferred to the wings 10.

In operation, and as previously described, an axial pushing force applied to piston stem 30 is transferred to the wings 10 of insert 1 by way of bearing surface 22. Accordingly, the axial force applied to piston stem 30 is transferred from insert 1 to the piston 2 so as to drive said piston distally (and in the direction of reference arrow 21) through carpule 20, whereby the fluid contents of the carpule may be expulsed by way of a hypodermic needle cannula (not shown), which communicates fluidically with the carpule at the distal end thereof.

It may be appreciated that the wings 10 of the piston stem insert 1 of this embodiment function as an anchor for the piston 2 to prevent an inadvertent and premature relocation of said piston through the carpule 20. However, and by virtue of their flexible nature, the wings 10 of insert 1 may be selectively rotated by piston stem 30 so as to release the piston 2 and thereby permit a distal relocation of the piston through the carpule 20, whereby fluid medication may be expulsed therefrom.

Figure 8:
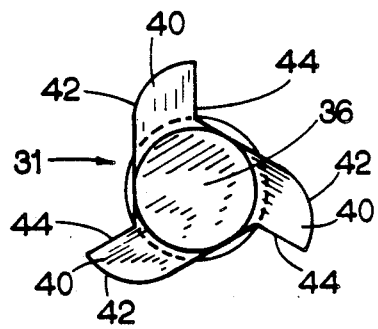
FIG. 8 is a bottom view of the piston stem insert of FIG. 7.
Figure 7:
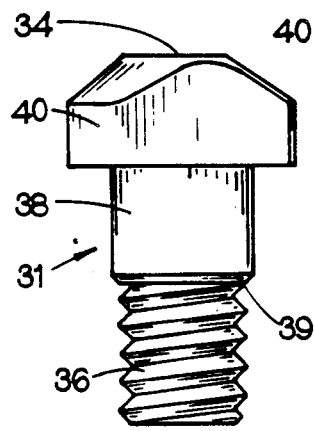
FIG. 7 is a side view of a piston stem insert which forms a second embodiment of the present invention.

A piston stem insert 31 which forms a second embodiment of the present invention is described while referring to FIGS. 7–12 of the drawings. As is best shown in FIGS. 7 and 8, the piston stem insert 31 includes a plug or head 34 formed at one end thereof and a screw threaded rod 36 formed at the opposite end. A cylindrical shank 38 extends between the head 34 and threaded rod 36. A tapered neck 39 extends around the periphery of the insert 31 at the intersection of threaded rod 36 and shank 38 to perform an important function, the details of which will soon be described. A series of anti-rotation wings 40 project radially outward and in different directions from the head 34 of insert 31. Although a total of three wings 40 are shown and described, it is to be understood that any number of such wings may project radially outward from head 34.

Each wing 40 is characterized by a rounded shoulder 42 facing in one direction and a square shoulder 44 facing in the opposite direction. As will be described in greater detail when referring to FIGS. 11 and 12, the rounded and squared shoulders 42 and 44 of each wing 40 help to control the ability of the piston stem insert 31 to rotate within a correspondingly shaped hollow receptacle (designated 46 in FIG. 10) that is molded into a piston 32.

Figure 9:
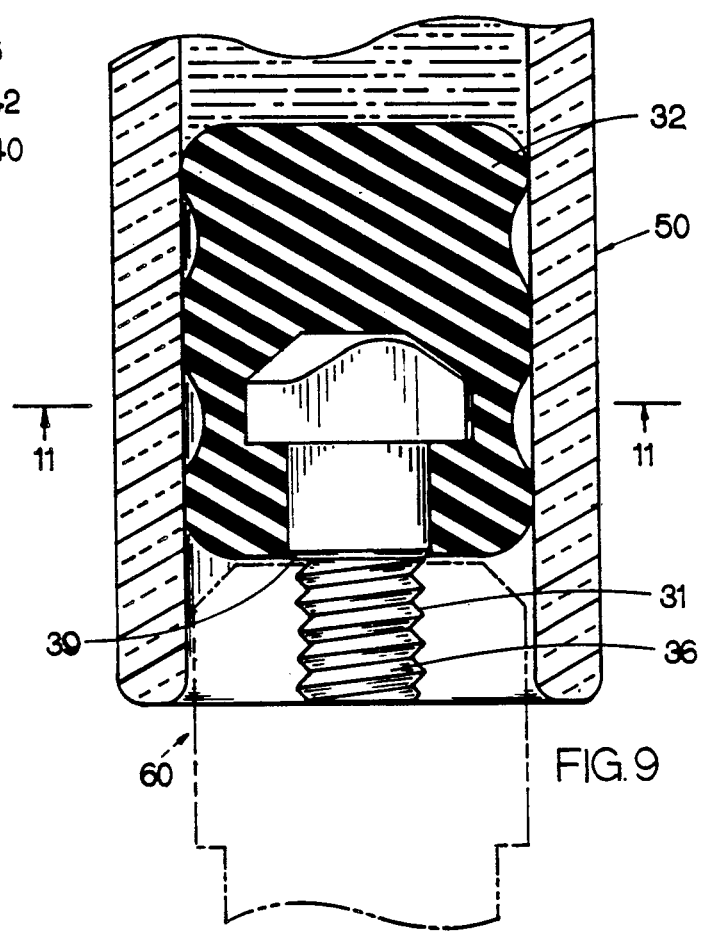
FIG. 9 is a partial cross-section showing a combination of the piston stem insert of FIG. 7 and an associated piston received within a fluid filled carpule.
Figure 10:
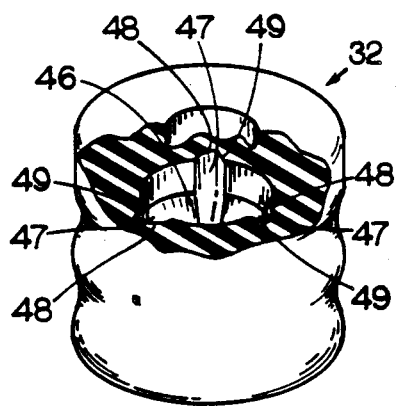
FIG. 10 is a partial cross-section of the piston of FIG. 9 to illustrate the hollow receptacle which is molded therein to receive the piston stem insert.
Figure 11:
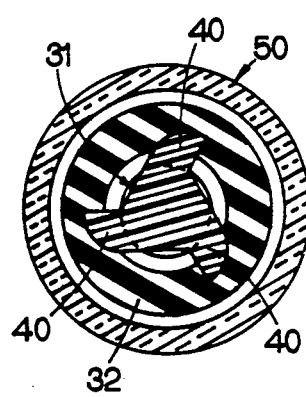
FIG. 11 is a cross-section taken along lines 11—11 of FIG. 9.

Referring now to FIGS. 9 and 11 of the drawings, a carpule 50 is illustrated in the as-packaged configuration with the piston 32 located at the proximal end thereof and the piston stem insert 31 pressed into and retained within the hollow receptacle of the piston, such that the threaded rod 36 of insert 31 is aligned for receipt within a correspondingly screw threaded receptacle of a piston stem (shown in phantom in FIG. 9 and designated 60).

As earlier disclosed, the hollow receptacle 46 of piston 32, within which the insert 31 is received, conforms to the shape of said insert. More particularly, and referring briefly to FIG. 10 of the drawings, the receptacle 46 of piston 32 is shown including a plurality of asymmetrical cavities 47. The number and alignment of the cavities 47 of receptacle 46 corresponds to the number and alignment of the wings (40 in FIG. 8) of the insert 31. That is to say, and referring concurrently to FIGS. 7, 8 and 10, each cavity 47 has a generally rounded wall 48 which conforms to the shape of the rounded shoulder 42 of insert 31 and which is skewed or misaligned relative to the center of receptacle 46 and an opposite flat wall 49 which conforms to the shape of the squared shoulder 44 of insert 31 and is axially aligned with the center of receptacle 46. Thus, in the as-packaged configuration of FIGS. 9 and 11, with the piston stem insert 31 pressed into the receptacle 46 of piston 32, each of the wings 40 of insert 31 will be received within a respective cavity 47 to securely retain the piston stem insert 31 within the piston.

Figure 12:
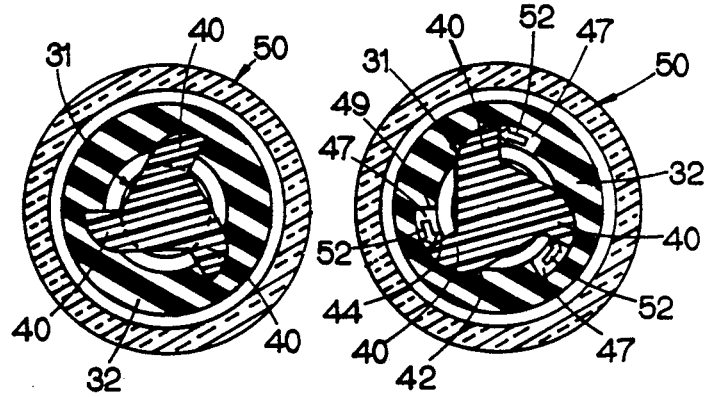
FIG. 12 shows the cross-section of FIG. 11 with the piston stem insert being rotated within the piston receptacle.

The rotation control features of the piston stem insert 31 of the present embodiment are now described while referring concurrently to FIGS. 9 and 12 of the drawings. In order to activate the carpule 50 so that the piston 32 can be driven therethrough to expulse fluid medication, the piston stem 60 is rotated into mating engagement with the threaded rod 36 of piston stem insert 31. The axial distance traveled by piston stem 60 along rod 36 is limited by the presence of the tapered neck 39 which extends around the periphery of insert 31. When the piston stem 60 is fully tightened against the piston stem insert 31, any further rotation of the piston stem and the torque generated thereby will cause a corresponding and continuous rotation of the insert through the receptacle (46 in FIG. 10) of piston 32. More particularly, the rotational force applied to piston stem 60 is transferred to insert 31 and to the wings 40 thereof such that the rounded shoulders 42 of said wings compress the rounded walls (48 in FIG. 10) of and deform the respective cavities 47 of receptacle 46 (best illustrated in FIG. 12). That is to say, the rounded walls of cavities 47 offer little resistance to the displacement of the wings 40 through cavities 47 when the piston stem insert 31 is rotated in a clockwise direction (indicated by the direction of reference arrows 52 in FIG. 12). Accordingly, the wings 40 will jump or skip from one cavity 47 to the next when the rotational force applied to piston stem 60 is sufficient to overcome the resistance encountered by the rounded shoulders 42 of wings 40 at the rounded cavity walls 48.

The piston 32 may now be driven axially and distally through carpule 50 so as to expluse the fluid contents thereof via a hypodermic needle cannula (not shown) which communicates fluidically with the distal end of said carpule. The piston stem 60 is then rotated in a counter-clockwise direction (opposite to the direction indicated by the reference arrows 52 in FIG. 12) so as to detach said stem from the screw threaded rod 36 of piston stem insert 31. More particularly, the counter-clockwise rotational force applied to piston stem 60 is again transferred to insert 31 and to the wings 40 thereof, such that the squared shoulders 44 of said wings are rotated into face-to-face contact with the flat walls (49 in FIG. 10) of the cavities 47 of receptacle 46. The flat walls of cavities 47 form a stop and thereby offer a relatively large resistance to the displacement of the wings 40 through cavities 47 when the piston stem insert 31 is rotated in the counter-clockwise direction. That is to say, the wings 40 will be blocked from rotating out of their respective cavities 47 by virtue of the resistance encountered by the squared shoulders 44 thereof against the flat cavity walls 49. In this manner, the piston stem insert 31 will be unable to rotate relative to piston 32 so that the piston stem 60 can be easily and reliably detached from insert 31.

It may be appreciated that by virtue of the shape of the opposing rounded and flat shoulders 42 and 44 of the wings 40 relative to the shape of the rounded and flat walls 48 and 49 of the receptacle cavities 47, the piston stem insert 31 of this embodiment is capable of rotation in only a single (i.e. clockwise) direction for the purpose of interconnecting a piston stem 60 with a piston 30. The ability of the piston stem insert 31 to rotate freely within a receptacle 46 of the piston 32 avoids the possibility that the piston stem insert could, as in conventional carpule based systems, be driven through and become embedded within its piston in the event that the piston stem were to be screwed down too tightly. Thus, not only might the piston be damaged (i.e. expanded), in such a conventional system, making it harder to drive the piston through the carpule, but the process of detaching the piston stem from its insert could also be made more difficult.

A piston stem insert 61 which forms a third embodiment of the present invention is described while referring concurrently to FIGS. 13-16 of the drawings. The piston stem insert 61 of FIGS. 13-16 is generally the same as the insert 31 described when referring to FIGS. 7-12. Thus, insert 61 includes a plurality of radially extending anti-rotation wings 64 at one end thereof for receipt within and rotation in a single direction through respective cavities 67 of a receptacle 68 that is molded into a piston 62 and a screw threaded rod 67 at the opposite end to be mated to a detachable piston stem (not shown). Moreover, each wing 64 of insert 61 includes a rounded shoulder 65 and an opposite facing squared shoulder 66.

The receptacle 68, in which the wings 64 of piston stem insert 61 are received and retained, is shaped so as to permit the wings 64 to self-align with respective asymmetrical cavities 67 of the receptacle 68 of piston 62 to permit a relatively easy and reliable press fit of the piston stem insert 61 into said receptacle 68 during the process by which insert 61 is installed within the piston.

Figure 14:
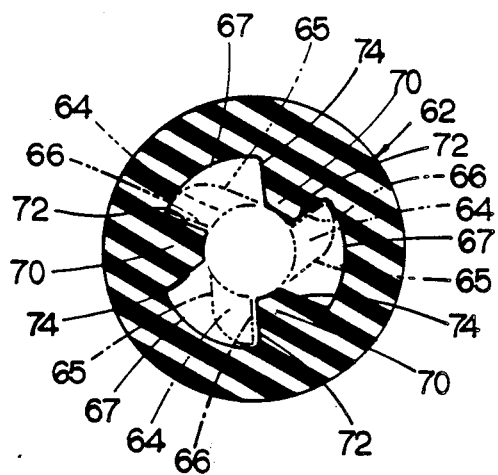
FIG. 14 is a cross-section taken along lines 14—14 of FIG. 13.
Figure 13:
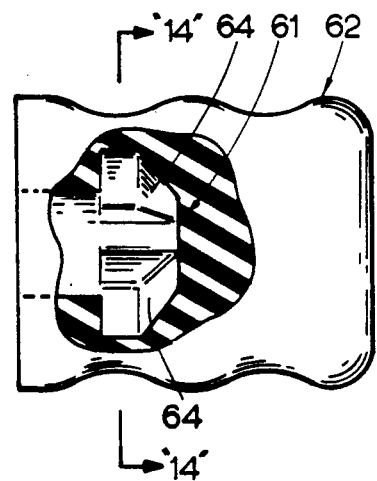
FIG. 13 is a partial cross-section showing a combination piston and a piston stem insert which forms a third embodiment of the present invention.
Figure 15:
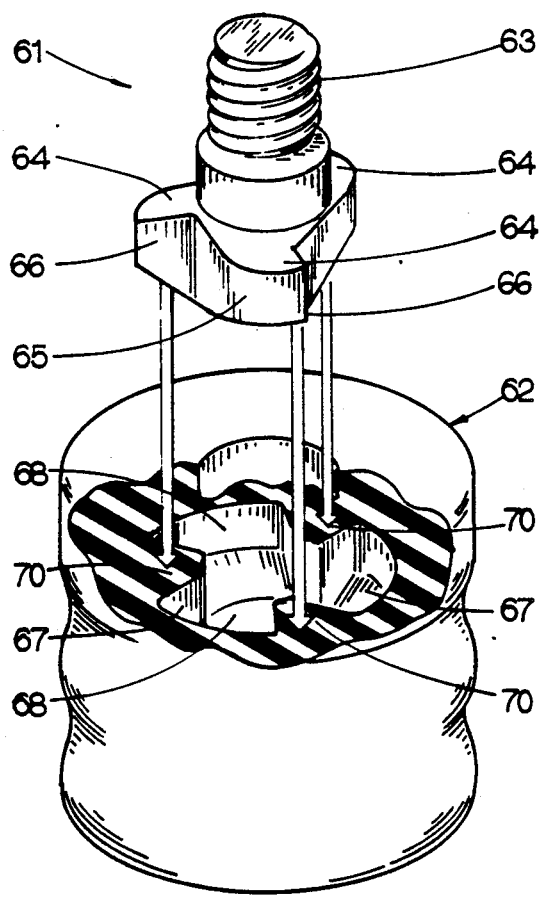
FIGS. 15 and 16 are illustrative of the self-aligning features of the piston of FIG. 13 for guiding the piston stem insert into receipt by a receptacle which is molded within said piston.

More particularly, the size of the cavities 67 of the receptacle 68 in piston 62 is increased so as to be larger than the corresponding size of the wings 64 which are to be received therein, such that piston 62 is provided with a series of relatively narrow, radially extending teeth 70. Each tooth 70 of piston 62 is located between a pair of successive cavities 67, so that teeth 70 are evenly spaced from one another around the piston 62. As is best shown in FIG. 14, each cavity 67 of the receptacle 68 is provided with a wall 72 which is axially aligned with the center of receptacle 68 and an opposing wall 74 which is skewed or misaligned relative to the center of receptacle 68.

Figure 16:
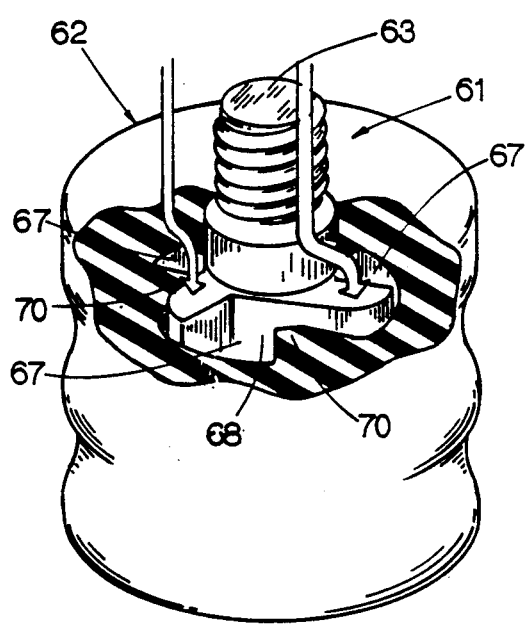

During the installation of piston stem insert 61 into the receptacle 68 of piston 62, the insert is press fit or forced inwardly (in the direction of the reference arrows of FIG. 15) into said receptacle. In the event that the wings 64 of insert 61 happen to be aligned with the cavities 67 of receptacle 68, then such wings 64 are merely received within and retained by said cavities. However, in the alternative event that wings 64 are misaligned with cavities 67, such that the wings contact respective ones of the radially extending teeth 70 of the piston 62, the relatively narrow dimension of the teeth 70 will automatically bias the wings 64 towards the cavities 67. That is to say, and as best shown in FIG. 16, the wings 64 of insert 61 which impact teeth 70 under an axially applied insertion force, will slide off and rotate with respect to said teeth so as to be reliably guided into receipt by respective cavities 67 of the receptacle 68 in piston 62.

The rotation control features and advantages of the piston stem insert 61 of this embodiment are similar to those which were previously described when referring to the insert 31 of FIGS. 7-12. Briefly, however, the piston stem insert 61 of FIGS. 13-16 is capable of rotation in a single (i.e. clockwise) direction through the receptacle 68 of piston 62 during the attachment of a piston stem to the rod end 67 of insert 61. That is, during the attachment of the piston stem, the rounded shoulders 65 of wings 64 are rotated into engagement with the walls 74 of cavities 67. Because of their skewed alignment with the center of receptacle 68, cavity walls 74 offer little resistance to the displacement of the wings 64 through receptacle 68 when the piston stem insert 61 is rotated in the clockwise direction in response to a rotational force applied thereto from the piston stem. However, the squared shoulders 66 of wings 64 will be rotated into engagement with the opposing walls 72 of cavities 67 when the insert is rotated in a counter-clockwise direction in order to detach the piston stem. Because of their alignment with the center of receptacle 68, cavity walls 72 form a stop and thereby offer a relatively large resistance to the displacement of wings 64 through receptacle 68 when the piston stem insert 61 is rotated in the counter-clockwise direction in response to a rotational force applied thereto from the piston stem. Accordingly, and by virtue of piston stem insert 61, a piston stem may be easily attached to or removed from a piston without the risk of damaging the piston and possibly impeding the delivery of fluid medication from the associated carpule.

It will be apparent that while a preferred embodiment of the invention has been shown and described, various modifications may be made without departing from the true spirit and scope of the invention. For example, while the piston stem inserts of this invention have been described as having particular application to a carpule based piston, it is to be understood that the teachings hereof are also applicable to a syringe based piston. In this case, the piston stem inserts herein described would permit a piston stem to be attached to or detached from a piston that is located in and moved through the cylinders of either a conventional syringe or a fluid collection device.

Having thus set forth a preferred embodiment of the invention, what is claimed is:

1. A combination piston having a hollow receptacle formed therein and a piston stem insert having a first end to be received at the receptacle of said piston and a second end to be engaged by a piston stem for interconnecting the piston stem with said piston so that said piston can be moved by the piston stem through the interior of a cylinder in which said piston is located;

the first end of said piston stem insert including at least one radially extending projection, and the receptacle of said piston including at least one cavity to receive the radial projection of said piston stem insert when the first end of said insert is received at the receptacle of said piston, said at least one cavity having a first end wall which is adapted to permit said radial projection to be rotated in a first direction past said end wall and out of said cavity when the piston stem is rotated in said first direction and into engagement with the second end of said piston stem insert to connect said stem to said piston, and said cavity having a second end wall which is adapted to prevent the rotation of said radial projection in an opposite direction and out of said cavity when the piston stem is rotated in said opposite direction so as to disconnect said stem from said piston.

2. The combination piston and piston stem insert recited in claim 1, wherein the first end wall of said receptacle cavity is transversely aligned with respect to the first direction in which the first end of said piston stem insert is to be rotated so as to permit the rotation of said projection past said first end wall and out of said cavity, and the second end wall of said cavity is perpendicularly aligned with respect to said opposite direction so as to block the rotation of said projection past said second end wall and out of said cavity.

3. The combination piston and piston stem insert recited in claim 1, wherein said piston receptacle has a plurality of radially and circumferentially spaced cavities and the first end of said piston stem insert has a plurality of radially projecting wings, said wings being received within respective cavities when the first end of piston stem insert is received at said piston receptacle.

4. The combination piston and piston stem insert recited in claim 3, wherein each of said plurality of cavities has a first end wall which is adapted to permit the rotation of said wings in said first direction out of their respective receptacle cavities when the piston stem is rotated in said first direction and into adjacently located cavities and a second end wall which is adapted to block the rotation of said wings in said opposite direction out of their respective cavities when said piston stem is rotated in said opposite direction.

5. The combination piston and piston stem insert recited in claim 3, wherein said plurality of cavities of said piston receptacle are larger than the respective wings which are to be received therewithin, the intermediate regions of said piston that are located between adjacent cavities being adapted to automatically realign said wings for receipt by said cavities in the event that said wings are aligned with and contact said intermediate regions when the first end of said piston stem insert is inserted into said piston receptacle.

6. A combination piston having a hollow receptacle formed therein and a piston stem insert having a first end to be received at said piston receptacle and a second end to be interconnected with a piston stem, said piston receptacle having a plurality of radially extending and circumferentially spaced cavities and the first end of said piston stem insert having a plurality of radially projecting wings, said wings being received within respective cavities when the first end of said piston stem insert is received at said piston receptacle, and the intermediate regions of said piston that are located between adjacent cavities of said piston receptacle are of particular size to automatically realign said wings for receipt by respective cavities in the event that said wings are aligned with and contact said intermediate regions when the first end of said piston stem insert is inserted into said piston receptacle.

7. The combination piston and piston stem insert recited in claim 6, wherein said plurality of cavities are larger than the respective wings which are to be received therewithin so as to reduce the size of said intermediate regions between said cavities and thereby automatically realign said wings for receipt by said cavities.

8. The combination piston and piston stem insert recited in claim 6, wherein each of said receptacle cavities includes means by which to permit the wings of the first end of said piston stem insert to be removed therefrom and rotated into adjacent cavities when the piston stem is rotated in a first direction and to prevent the removal of said wings from said cavities when the piston stem is rotated in an opposite direction.

9. In combination, a piston stem insert to be interconnected with a piston that is located within a fluid filled cylinder and a piston stem to be attached to said piston stem insert when said insert is connected to the piston to relocate said piston through the cylinder;

said piston stem insert including flexible retaining means extending therefrom so as to frictionally engage the cylinder and prevent a relocation of the piston through the cylinder, and said piston stem having a bearing surface projecting therefrom, said bearing surface being moved into contact with the flexible retaining means of said piston stem insert when said piston stem is attached to said insert for causing said retaining means to be displaced out of frictional engagement with the cylinder such that an axial force applied to said piston stem is transferred to the piston by way of said piston stem insert to permit said piston to be relocated through the cylinder.

10. The combination recited in claim 9, including hinge means located between said piston stem insert and said flexible retaining means thereof to permit said retaining means to rotate at said hinge means out of frictional engagement with the cylinder when the bearing surface of said piston stem is moved into contact with said retaining means.

11. The combination recited in claim 9, wherein said flexible retaining means includes at least two wings projecting radially outward from said piston stem insert towards the cylinder.

12. The combination recited in claim 9, wherein the bearing surface of said piston stem is a flared head that projects outwardly from said piston stem to contact the retaining means of said piston stem insert when said stem is attached to said insert.

* * * * *